(12) United States Patent
Frushour et al.

(10) Patent No.: US 11,576,697 B2
(45) Date of Patent: Feb. 14, 2023

(54) ELECTROSURGICAL FORCEPS FOR VIDEO ASSISTED THORACOSCOPIC SURGERY AND OTHER SURGICAL PROCEDURES

(71) Applicant: Covidien LP, Mansfield, MA (US)

(72) Inventors: Scott E. Frushour, Boulder, CO (US); Eric R. Larson, Boulder, CO (US)

(73) Assignee: Covidien LP, Mansfield, MA (US)

( * ) Notice: Subject to any disclaimer, the term of this patent is extended or adjusted under 35 U.S.C. 154(b) by 346 days.

(21) Appl. No.: 16/860,360

(22) Filed: Apr. 28, 2020

(65) Prior Publication Data

US 2020/0253630 A1    Aug. 13, 2020

Related U.S. Application Data

(63) Continuation of application No. 15/671,200, filed on Aug. 8, 2017, now Pat. No. 10,631,887.

(Continued)

(51) Int. Cl.
*A61B 18/08* (2006.01)
*A61B 17/32* (2006.01)
(Continued)

(52) U.S. Cl.
CPC ............ *A61B 17/320016* (2013.01); *A61B 17/00234* (2013.01); *A61B 17/2909* (2013.01);
(Continued)

(58) Field of Classification Search
CPC ............. A61B 17/2909; A61B 18/085; A61B 18/1445; A61B 2017/2936; A61B 17/2946; A61B 17/29; Y10T 29/53257
(Continued)

(56) References Cited

U.S. PATENT DOCUMENTS

D249,549 S   9/1978  Pike
D263,020 S   2/1982  Rau, III
(Continued)

FOREIGN PATENT DOCUMENTS

CN   201299462 Y   9/2009
CN   202086577 U   12/2011
(Continued)

OTHER PUBLICATIONS

McLellan et al. "Vessel Sealing for Hemostasis During Gynecologic Surgery" Sales/Product Literature 1999.
(Continued)

*Primary Examiner* — Donghai D Nguyen
(74) *Attorney, Agent, or Firm* — Carter, DeLuca & Farrell LLP

(57) ABSTRACT

A surgical instrument includes a shaft defining an axis, an end effector coupled to a distal portion thereof, a fixed handle coupled to a proximal portion thereof, a drive bar, a movable handle, and a linkage. The drive bar is disposed within the shaft and operably coupled to the end effector. The movable handle is movable relative to the fixed handle between open and closed positions and is coupled to the drive bar via a first pin on the axis. The linkage includes a first end portion coupled to the movable handle via a second pin and a second end portion coupled to the shaft via a third pin on the axis. In the closed position of the movable handle, the second pin is disposed in a near-over-center position relative to the axis to reduce a force necessary to maintain the movable handle in the closed position.

16 Claims, 6 Drawing Sheets

Related U.S. Application Data

(60) Provisional application No. 62/374,989, filed on Aug. 15, 2016.

(51) Int. Cl.
    *A61B 17/00*      (2006.01)
    *A61B 17/29*      (2006.01)
    *A61B 18/14*      (2006.01)
    *A61B 34/30*      (2016.01)
    *A61B 34/35*      (2016.01)

(52) U.S. Cl.
    CPC ........ *A61B 18/085* (2013.01); *A61B 18/1445* (2013.01); *A61B 34/35* (2016.02); *A61B 2017/2936* (2013.01); *A61B 2034/302* (2016.02)

(58) Field of Classification Search
    USPC .......................................................... 29/758
    See application file for complete search history.

(56) References Cited

U.S. PATENT DOCUMENTS

| | | | |
|---|---|---|---|
| D295,893 | S | 5/1988 | Sharkany et al. |
| D295,894 | S | 5/1988 | Sharkany et al. |
| 4,763,669 | A | 8/1988 | Jaeger |
| D298,353 | S | 11/1988 | Manno |
| D299,413 | S | 1/1989 | DeCarolis |
| 5,100,420 | A | 3/1992 | Green et al. |
| 5,258,001 | A | 11/1993 | Corman |
| D343,453 | S | 1/1994 | Noda |
| 5,304,203 | A | 4/1994 | El-Mallawany et al. |
| 5,308,357 | A | 5/1994 | Lichtman |
| D348,930 | S | 7/1994 | Olson |
| D349,341 | S | 8/1994 | Lichtman et al. |
| 5,344,424 | A | 9/1994 | Roberts et al. |
| D354,564 | S | 1/1995 | Medema |
| D358,887 | S | 5/1995 | Feinberg |
| 5,540,685 | A | 7/1996 | Parins et al. |
| 5,578,052 | A | 11/1996 | Koros et al. |
| 5,611,808 | A | 3/1997 | Hossain et al. |
| 5,618,294 | A | 4/1997 | Aust et al. |
| D384,413 | S | 9/1997 | Zlock et al. |
| 5,665,100 | A | 9/1997 | Yoon |
| 5,752,644 | A | 5/1998 | Bolanos et al. |
| H1745 | H | 8/1998 | Paraschac |
| 5,814,043 | A | 9/1998 | Shapeton |
| D402,028 | S | 12/1998 | Grimm et al. |
| D408,018 | S | 4/1999 | McNaughton |
| 5,913,874 | A | 6/1999 | Berns et al. |
| 5,960,544 | A | 10/1999 | Beyers |
| D416,089 | S | 11/1999 | Barton et al. |
| 6,050,996 | A | 4/2000 | Schmaltz et al. |
| D424,694 | S | 5/2000 | Tetzlaff et al. |
| D425,201 | S | 5/2000 | Tetzlaff et al. |
| H1904 | H | 10/2000 | Yates et al. |
| 6,293,954 | B1 | 9/2001 | Fogarty et al. |
| D449,886 | S | 10/2001 | Tetzlaff et al. |
| 6,329,778 | B1 | 12/2001 | Culp et al. |
| 6,334,861 | B1 | 1/2002 | Chandler et al. |
| D453,923 | S | 2/2002 | Olson |
| D454,951 | S | 3/2002 | Bon |
| D457,958 | S | 5/2002 | Dycus et al. |
| D457,959 | S | 5/2002 | Tetzlaff et al. |
| 6,406,485 | B1 | 6/2002 | Hossain et al. |
| H2037 | H | 7/2002 | Yates et al. |
| 6,464,704 | B2 | 10/2002 | Schmaltz et al. |
| D465,281 | S | 11/2002 | Lang |
| D466,209 | S | 11/2002 | Bon |
| 6,511,480 | B1 | 1/2003 | Tetzlaff et al. |
| 6,673,092 | B1 | 1/2004 | Bacher |
| D493,888 | S | 8/2004 | Reschke |
| D496,997 | S | 10/2004 | Dycus et al. |
| D499,181 | S | 11/2004 | Dycus et al. |
| D502,994 | S | 3/2005 | Blake, III |
| D509,297 | S | 9/2005 | Wells |
| D525,361 | S | 7/2006 | Hushka |
| D531,311 | S | 10/2006 | Guerra et al. |
| 7,118,570 | B2 | 10/2006 | Tetzlaff et al. |
| D533,274 | S | 12/2006 | Visconti et al. |
| D533,942 | S | 12/2006 | Kerr et al. |
| D535,027 | S | 1/2007 | James et al. |
| D538,932 | S | 3/2007 | Malik |
| D541,418 | S | 4/2007 | Schechter et al. |
| D541,611 | S | 5/2007 | Aglassinger |
| D541,938 | S | 5/2007 | Kerr et al. |
| D545,432 | S | 6/2007 | Watanabe |
| D547,154 | S | 7/2007 | Lee |
| 7,329,257 | B2 | 2/2008 | Kanehira et al. |
| D564,662 | S | 3/2008 | Moses et al. |
| D567,943 | S | 4/2008 | Moses et al. |
| D575,395 | S | 8/2008 | Hushka |
| D575,401 | S | 8/2008 | Hixson et al. |
| 7,431,730 | B2 | 10/2008 | Viola |
| D582,038 | S | 12/2008 | Swoyer et al. |
| 7,641,653 | B2 | 1/2010 | Dalla Betta et al. |
| D617,900 | S | 6/2010 | Kingsley et al. |
| D617,901 | S | 6/2010 | Unger et al. |
| D617,902 | S | 6/2010 | Twomey et al. |
| D617,903 | S | 6/2010 | Unger et al. |
| D618,798 | S | 6/2010 | Olson et al. |
| D621,503 | S | 8/2010 | Otten et al. |
| D627,462 | S | 11/2010 | Kingsley |
| D628,289 | S | 11/2010 | Romero |
| D628,290 | S | 11/2010 | Romero |
| 7,854,185 | B2 | 12/2010 | Zhang et al. |
| D630,324 | S | 1/2011 | Reschke |
| 7,896,878 | B2 | 3/2011 | Johnson et al. |
| D649,249 | S | 11/2011 | Guerra |
| D649,643 | S | 11/2011 | Allen, IV et al. |
| 8,147,489 | B2 | 4/2012 | Moses et al. |
| D661,394 | S | 6/2012 | Romero et al. |
| 8,298,233 | B2 | 10/2012 | Mueller |
| D670,808 | S | 11/2012 | Moua et al. |
| 8,366,709 | B2 | 2/2013 | Schechter et al. |
| 8,394,096 | B2 | 3/2013 | Moses et al. |
| D680,220 | S | 4/2013 | Rachlin |
| 8,409,246 | B2 | 4/2013 | Kerr et al. |
| 8,409,247 | B2 | 4/2013 | Garrison et al. |
| 8,425,504 | B2 | 4/2013 | Orton et al. |
| 8,425,511 | B2 | 4/2013 | Olson |
| 8,430,877 | B2 | 4/2013 | Kerr et al. |
| 8,439,913 | B2 | 5/2013 | Horner et al. |
| 8,469,716 | B2 | 6/2013 | Fedotov et al. |
| 8,469,991 | B2 | 6/2013 | Kerr |
| 8,469,992 | B2 | 6/2013 | Roy et al. |
| 8,480,671 | B2 | 7/2013 | Mueller |
| 8,491,624 | B2 | 7/2013 | Kerr et al. |
| 8,491,625 | B2 | 7/2013 | Horner |
| 8,491,626 | B2 | 7/2013 | Roy et al. |
| 8,512,336 | B2 | 8/2013 | Couture |
| 8,540,749 | B2 | 9/2013 | Garrison et al. |
| 8,551,091 | B2 | 10/2013 | Couture et al. |
| 8,556,929 | B2 | 10/2013 | Harper et al. |
| 8,568,397 | B2 | 10/2013 | Horner et al. |
| 8,568,408 | B2 | 10/2013 | Townsend et al. |
| 8,585,736 | B2 | 11/2013 | Horner et al. |
| 8,591,510 | B2 | 11/2013 | Allen, IV et al. |
| 8,597,295 | B2 | 12/2013 | Kerr |
| 8,623,018 | B2 | 1/2014 | Horner et al. |
| 8,628,557 | B2 | 1/2014 | Collings et al. |
| 8,641,712 | B2 | 2/2014 | Couture |
| 8,647,343 | B2 | 2/2014 | Chojin et al. |
| 8,652,135 | B2 | 2/2014 | Nau, Jr. |
| 8,663,222 | B2 | 3/2014 | Anderson et al. |
| 8,672,939 | B2 | 3/2014 | Garrison |
| 8,679,098 | B2 | 3/2014 | Hart |
| 8,685,009 | B2 | 4/2014 | Chernov et al. |
| 8,685,021 | B2 | 4/2014 | Chernov et al. |
| 8,685,056 | B2 | 4/2014 | Evans et al. |
| 8,702,737 | B2 | 4/2014 | Chojin et al. |
| 8,702,749 | B2 | 4/2014 | Twomey |
| 8,734,445 | B2 | 5/2014 | Johnson et al. |

(56) References Cited

U.S. PATENT DOCUMENTS

| | | |
|---|---|---|
| 8,740,898 B2 | 6/2014 | Chojin et al. |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,858,553 B2 | 10/2014 | Chojin |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,888,775 B2 | 11/2014 | Nau, Jr. et al. |
| 8,898,888 B2 | 12/2014 | Brandt et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,359 B2 | 3/2015 | Kerr et al. |
| 9,005,200 B2 | 4/2015 | Roy et al. |
| 9,017,372 B2 | 4/2015 | Artale et al. |
| 9,028,484 B2 | 5/2015 | Craig |
| 9,028,492 B2 | 5/2015 | Kerr et al. |
| 9,028,495 B2 | 5/2015 | Mueller et al. |
| 9,039,704 B2 | 5/2015 | Joseph |
| 9,039,732 B2 | 5/2015 | Sims et al. |
| 9,084,608 B2 | 7/2015 | Larson et al. |
| 9,113,933 B2 | 8/2015 | Chernova et al. |
| 9,113,934 B2 | 8/2015 | Chernov et al. |
| 9,113,938 B2 * | 8/2015 | Kerr ............... A61B 17/29 |
| 9,161,807 B2 | 10/2015 | Garrison |
| 9,211,657 B2 | 12/2015 | Ackley et al. |
| 9,265,568 B2 | 2/2016 | Chernov et al. |
| 9,333,002 B2 | 5/2016 | Garrison |
| 9,381,059 B2 | 7/2016 | Garrison |
| 9,456,870 B2 | 10/2016 | Chernov et al. |
| 9,498,278 B2 | 11/2016 | Couture et al. |
| 9,498,279 B2 | 11/2016 | Artale et al. |
| 9,504,519 B2 | 11/2016 | Kerr et al. |
| 9,585,709 B2 | 3/2017 | Krapohl |
| 9,615,877 B2 | 4/2017 | Tyrrell et al. |
| 9,655,672 B2 | 5/2017 | Artale et al. |
| 10,631,887 B2 | 4/2020 | Frushour et al. |
| 2003/0018332 A1 | 1/2003 | Schmaltz et al. |
| 2003/0109875 A1 | 6/2003 | Tetzlaff et al. |
| 2003/0199869 A1 | 10/2003 | Johnson et al. |
| 2003/0220637 A1 | 11/2003 | Truckai et al. |
| 2003/0229344 A1 | 12/2003 | Dycus et al. |
| 2004/0092927 A1 | 5/2004 | Podhajsky et al. |
| 2005/0070889 A1 | 3/2005 | Nobis et al. |
| 2005/0107784 A1 | 5/2005 | Moses et al. |
| 2005/0113826 A1 | 5/2005 | Johnson et al. |
| 2005/0113828 A1 | 5/2005 | Shields et al. |
| 2005/0119655 A1 | 6/2005 | Moses et al. |
| 2005/0159745 A1 | 7/2005 | Truckai et al. |
| 2006/0253126 A1 | 11/2006 | Bjerken et al. |
| 2007/0062017 A1 | 3/2007 | Dycus et al. |
| 2007/0088356 A1 | 4/2007 | Moses et al. |
| 2007/0179499 A1 | 8/2007 | Garrison |
| 2007/0260241 A1 | 11/2007 | Dalla Betta et al. |
| 2008/0215048 A1 | 9/2008 | Hafner et al. |
| 2009/0131934 A1 | 5/2009 | Odom et al. |
| 2009/0171353 A1 | 7/2009 | Johnson et al. |
| 2009/0182327 A1 | 7/2009 | Unger |
| 2009/0240246 A1 | 9/2009 | Deville et al. |
| 2009/0302090 A1 | 12/2009 | Shah |
| 2009/0308909 A1 | 12/2009 | Nalagatla et al. |
| 2010/0016857 A1 | 1/2010 | McKenna et al. |
| 2010/0130977 A1 | 5/2010 | Garrison et al. |
| 2010/0179540 A1 | 7/2010 | Marczyk et al. |
| 2010/0179545 A1 | 7/2010 | Twomey et al. |
| 2010/0179547 A1 | 7/2010 | Cunningham et al. |
| 2010/0228250 A1 | 9/2010 | Brogna |
| 2010/0274244 A1 | 10/2010 | Heard |
| 2010/0292691 A1 | 11/2010 | Brogna |
| 2010/0305567 A1 | 12/2010 | Swanson |
| 2011/0060314 A1 | 3/2011 | Wallace et al. |
| 2011/0060356 A1 | 3/2011 | Reschke et al. |
| 2011/0072638 A1 | 3/2011 | Brandt et al. |
| 2011/0087218 A1 | 4/2011 | Boudreaux et al. |
| 2011/0218530 A1 | 9/2011 | Reschke |
| 2011/0238065 A1 | 9/2011 | Hunt et al. |
| 2011/0238067 A1 | 9/2011 | Moses et al. |
| 2011/0257680 A1 | 10/2011 | Reschke et al. |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2012/0059372 A1 | 3/2012 | Johnson |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172873 A1 | 7/2012 | Artale et al. |
| 2012/0172924 A1 | 7/2012 | Allen, IV |
| 2012/0184989 A1 | 7/2012 | Twomey |
| 2012/0184990 A1 | 7/2012 | Twomey |
| 2012/0209263 A1 | 8/2012 | Sharp et al. |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0265241 A1 | 10/2012 | Hart et al. |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1 | 1/2013 | Sims et al. |
| 2013/0018411 A1 | 1/2013 | Collings et al. |
| 2013/0022495 A1 | 1/2013 | Allen, IV et al. |
| 2013/0030432 A1 | 1/2013 | Garrison et al. |
| 2013/0041370 A1 | 2/2013 | Unger |
| 2013/0046295 A1 | 2/2013 | Kerr et al. |
| 2013/0046303 A1 | 2/2013 | Evans et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1 | 4/2013 | Garrison |

(56) References Cited

U.S. PATENT DOCUMENTS

| | | |
|---|---|---|
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |
| 2013/0178852 A1 | 7/2013 | Allen, IV et al. |
| 2013/0185922 A1 | 7/2013 | Twomey et al. |
| 2013/0190753 A1 | 7/2013 | Garrison |
| 2013/0190760 A1 | 7/2013 | Allen, IV |
| 2013/0197503 A1 | 8/2013 | Orszulak |
| 2013/0226177 A1 | 8/2013 | Brandt |
| 2013/0296843 A1 | 11/2013 | Boudreaux et al. |
| 2014/0221994 A1 | 8/2014 | Reschke |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0066076 A1 | 3/2015 | Kerr et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2015/0223874 A1 | 8/2015 | Artale et al. |
| 2016/0157925 A1 | 6/2016 | Artale et al. |

FOREIGN PATENT DOCUMENTS

| | | |
|---|---|---|
| CN | 102525639 A | 7/2012 |
| DE | 2415263 A1 | 10/1975 |
| DE | 02514501 A1 | 10/1976 |
| DE | 2627679 A1 | 1/1977 |
| DE | 03423356 02 | 6/1986 |
| DE | 03612646 A1 | 4/1987 |
| DE | 3627221 A1 | 2/1988 |
| DE | 8712328 U1 | 2/1988 |
| DE | 04303882 02 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| EP | 2353535 A1 | 8/2011 |
| EP | 2436330 A1 | 4/2012 |
| JP | 61501068 A | 5/1986 |
| JP | 1147150 | 6/1989 |
| JP | 55106 | 1/1993 |
| JP | 0540112 A | 2/1993 |
| JP | 6121797 A | 5/1994 |
| JP | 6285078 A | 10/1994 |
| JP | 06343644 | 12/1994 |
| JP | 6511401 | 12/1994 |
| JP | H07265328 A | 10/1995 |
| JP | H0856955 A | 3/1996 |
| JP | 08252263 A | 10/1996 |
| JP | 8289895 A | 11/1996 |
| JP | 8317934 A | 12/1996 |
| JP | 8317936 A | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | H1024051 A | 1/1998 |
| JP | H1070124 A | 3/1998 |
| JP | 10155798 A | 6/1998 |
| JP | 1147149 | 2/1999 |
| JP | 11169381 A | 6/1999 |
| JP | 11192238 A | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | 0006030945 B2 | 11/2016 |
| JP | 6502328 B2 | 4/2019 |
| SU | 401367 A1 | 10/1973 |
| WO | 9400059 A1 | 1/1994 |
| WO | 9923933 A2 | 5/1999 |
| WO | 0024330 A1 | 5/2000 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 02080786 A1 | 10/2002 |
| WO | 02080793 A1 | 10/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |
| WO | 2013009758 A2 | 1/2013 |
| WO | 2013022928 A1 | 2/2013 |
| WO | 2016015233 A1 | 2/2016 |

(56) References Cited

FOREIGN PATENT DOCUMENTS

OTHER PUBLICATIONS

"Electrosurgery: A Historical Overview" Innovations in Electrosurgery; Sales/Product Literature; Dec. 31, 2000, 6 pages.
Johnson et al. "Evaluation of a Bipolar Electrothermal Vessel Sealing Device in Hemorrhoidectomy" Sales/Product Literature; Jan. 2004, 1 page.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Heniford et al. "Initial Results with an Electrothermal Bipolar Vessel Sealer" Surgical Endoscopy (2000) 15:799-801. (4 pages).
Notification of Transmittal of the International Search Report and the Written Opinion of the International Searching Authority, or the Declaration issuedin corresponding PCT application No. PCT/US2017/046019 dated Nov. 22, 2017, 12 pages.
"Reducing Needlestick Injuries in the Operating Room" Sales/Product Literature 2001. (1 page).
Levy et al., "Update on Hysterectomy—New Technologies and Techniques" OBG Management, Feb. 2003, 15 pages.
Barbara Levy, "Use of a New Vessel Ligation Device During Vaginal Hysterectomy" FIGO 2000, Washington, D.C. (1 page).
Vallfors et al., "Automatically Controlled Bipolar Electrocoagulation—COA-COMP", Neurosurg. Rev. (1984), pp. 187-190.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz, abandoned.
U.S. Appl. No. 09/591,328, filed Jun. 9, 2000, Thomas P. Ryan.
U.S. Appl. No. 12/336,970, filed Dec. 17, 2008, Paul R. Sremcich, abandoned.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas MedicalCenter, Charlotte, NC; Date: Aug. 2003.
Peterson et al., "Comparison of Healing Process Following Ligation with Sutures and Bipolar Vessel Sealing" Surgical Technology International (2001).
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al., "High-burst-strength, feedback-controlled bipolar vessel sealing" Surgical Endoscopy (1998) 12:876-878.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Herman et al., "Laparoscopic Intestinal Resection With the LigaSure Vessel Sealing System: A Case Report" Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, Dated: 2005.

(56) References Cited

OTHER PUBLICATIONS

McLellan et al., "Vessel Sealing for Hemostasis During Pelvic Surgery" Int'l Federation of Gynecology and Obstetrics FIGO World Congress 2000, Washington, DC.

* cited by examiner

ELECTROSURGICAL FORCEPS FOR VIDEO ASSISTED THORACOSCOPIC SURGERY AND OTHER SURGICAL PROCEDURES

CROSS REFERENCE TO RELATED APPLICATION

This application is a continuation application of U.S. patent application Ser. No. 15/671,200, filed on Aug. 8, 2017, now U.S. Pat. No. 10,631,887, which claims the benefit of and priority to U.S. Provisional Application Ser. No. 62/374,989, filed on Aug. 15, 2016 the entire contents of each of which are hereby incorporated herein by reference.

BACKGROUND

Technical Field

The present disclosure relates to surgical instruments and, more particularly, to an electrosurgical forceps configured for treating and/or cutting tissue in Video Assisted Thoracoscopic Surgery and other surgical procedures.

Background of Related Art

In minimally-invasive surgical procedures, operations are carried out within the body by elongated instruments inserted through small entrance openings in the body, either directly or through one or more access ports positioned within the entrance openings. Because the instrumentation and any required punctures or incisions are relatively small, minimally-invasive surgery is less invasive compared to conventional open surgical procedures. As a result, minimally-invasive surgery tends to minimizes trauma to the patient, reduce patient recovery time, and minimize hospital costs.

In minimally-invasive thoracic surgery, for example, access to the thoracic cavity as well as maneuverability within the thoracic cavity is limited since the access port is typically placed within the confined intercostal space between a patient's ribs. Such procedures, commonly referred to as Video Assisted Thoracoscopic Surgery (VATS), aim to reduce patient recovery time by accessing the thoracic cavity through the natural intercostal space without spreading the ribs as in open procedures. Procedures performed in this manner may include, for example, lung resection procedures.

Electrosurgical forceps utilize both mechanical clamping action and energy to treat, e.g., coagulate, cauterize, and/or seal, tissue. Typically, once tissue is treated, the treated tissue is divided by way of a knife or blade member incorporated into the electrosurgical forceps. Electrosurgical forceps are useful in VATS procedures such as, for example, lung resection procedures, where electrosurgical forceps may be utilized to treat and cut surrounding tissue, thus facilitating the isolation of lung tissue to be removed and reducing bleeding during the lung resection procedure.

It would therefore be advantageous to provide an electrosurgical forceps configured for use in VATS procedures and other surgical procedures, for example, to facilitate lung resection procedures.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with aspects of the present disclosure, a surgical instrument is provided. The surgical instrument includes an elongated shaft defining a longitudinal axis and including a proximal portion and a distal portion, an end effector assembly coupled to the distal portion of the elongated shaft, a fixed handle coupled to the proximal portion of the elongated shaft, a drive bar, a movable handle, and a linkage. The drive bar is slidably disposed within the elongated shaft and operably coupled to the end effector assembly such that translation of the drive bar through the elongated shaft manipulates the end effector assembly. The movable handle is movable relative to the fixed handle between an open position and a closed position to translate the drive bar through the elongated shaft. The movable handle, more specifically, is pivotably coupled to the drive bar via a first pivot pin. The first pivot pin is aligned on the longitudinal axis. The linkage includes a first end portion and a second end portion. The first end portion of the linkage is pivotably coupled to the movable handle via a second pivot pin, while the second end portion of the linkage is pivotably coupled to the elongated shaft via a third pivot pin. The third pivot pin is aligned on the longitudinal axis. In the closed position of the movable handle, the second pivot pin is disposed in a near-over-center position relative to the longitudinal axis to reduce a force necessary to maintain the movable handle in the closed position.

In an aspect of the present disclosure, the elongated shaft defines a cut-out disposed therein configured to receive at least a portion of the second pivot pin in the near-over-center position of the second pivot pin.

In another aspect of the present disclosure, the movable handle, the fixed handle, and/or the elongated shaft inhibits the second pivot pin from reaching an over-the-center position relative to the longitudinal axis.

In yet another aspect of the present disclosure, the end effector assembly includes first and second jaw members. In such aspects, translation of the drive bar through the elongated shaft moves the first and second jaw members between a spaced-apart position and an approximated position.

In still another aspect of the present disclosure, the near-over-center position of the second pivot pin corresponds to the approximated position of the first and second jaw members.

In still yet another aspect of the present disclosure, each of the first and second jaw members defines an electrically-conductive tissue-contacting surface adapted to connect to a source of energy. The tissue-contacting surfaces are configured to grasp tissue therebetween.

In another aspect of the present disclosure, the movable handle includes a clevis configured to couple at least a portion of the elongated shaft with at least a portion of the linkage. The first and second pivot pins extend within the clevis.

In another aspect of the present disclosure, the elongated shaft includes a pair of opposed slots defined therethrough. The first pivot pin extends through the opposed slots of the elongated shaft.

In still another aspect of the present disclosure, an activation assembly is disposed on the fixed handle or the movable handle. The activation assembly is selectively activatable to supply energy to the end effector assembly.

In yet another aspect of the present disclosure, the activation assembly is positioned such that the activation assembly is activated upon movement of the movable handle to the closed position.

In still yet another aspect of the present disclosure, the fixed handle and/or the movable handle includes a finger ring.

Another surgical instrument provided in accordance with aspects of the present disclosure includes an elongated shaft, an end effector assembly, a drive bar, a movable handle, and a linkage. The elongated shaft includes a proximal portion and a distal portion. The end effector assembly is coupled to the distal portion of the elongated shaft and includes first and second jaw members movable between a spaced-apart position and an approximated position. The drive bar is slidably disposed within the elongated shaft and operably coupled to the first jaw member and/or the second jaw member such that translation of the drive bar through the elongated shaft moves the first and second jaw members between the spaced-apart position and the approximated position. The movable handle is pivotably coupled to the drive bar via a first pivot pin and is movable between an open position and a closed position to translate the drive bar through the elongated shaft to thereby move the first and second jaw members between the spaced-apart position and the approximated position. The linkage includes a first end portion and a second end portion. The first end portion of the linkage is pivotably coupled to the movable handle via a second pivot pin. The second end portion of the linkage is pivotably coupled to the elongated shaft via a third pivot pin. In the closed position of the movable handle, the second pivot pin is disposed in a near-over-center position relative to the first pivot pin and the third pivot pin to reduce a force necessary to maintain the movable handle in the closed position.

In an aspect of the present disclosure, the elongated shaft defines a cut-out disposed therethrough configured to receive at least a portion of the second pivot pin in the near-over-center position of the second pivot pin.

In another aspect of the present disclosure, a fixed handle fixed relative to the elongated shaft is provided. In such aspects, the movable handle is movable relative to the fixed handle between the open and closed positions.

In still another aspect of the present disclosure, each of the first and second jaw members defines an electrically-conductive tissue-contacting surface adapted to connect to a source of energy. The tissue-contacting surfaces are configured to grasp tissue therebetween in the approximated position.

In yet another aspect of the present disclosure, the movable handle includes a clevis configured to couple at least a portion of the elongated shaft with at least a portion of the linkage. In such aspects, the first and second pivot pins extend within the clevis.

In another aspect of the present disclosure, the elongated shaft includes a pair of opposed slots defined therethrough. The first pivot pin extends through the opposed slots of the elongated shaft.

In still yet another aspect of the present disclosure, an activation assembly is disposed on the movable handle. The activation assembly is selectively activatable to supply energy to the first and second jaw members.

In another aspect of the present disclosure, the activation assembly is positioned such that the activation assembly is activated upon movement of the movable handle to the closed position.

In an aspect of the present disclosure, the movable handle includes a finger ring.

BRIEF DESCRIPTION OF THE DRAWINGS

Various aspects and features of the present disclosure are described herein with reference to the drawings, wherein.

DETAILED DESCRIPTION

Figure 1:
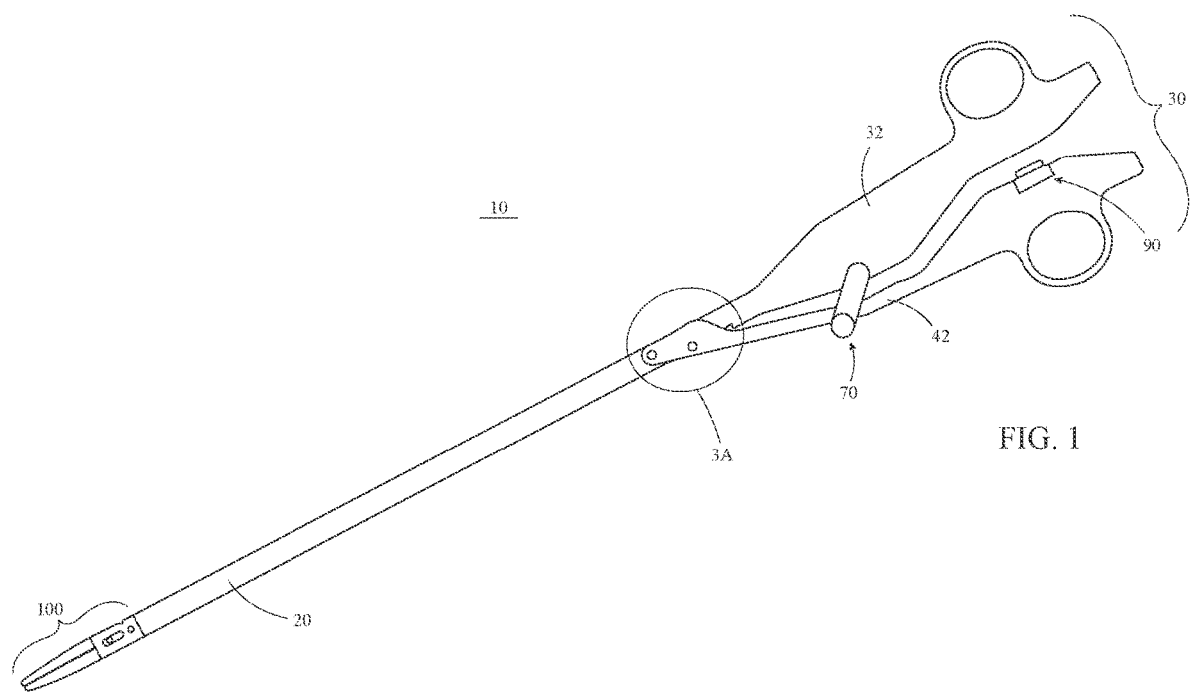
FIG. 1 is a side view of an electrosurgical forceps provided in accordance with aspects of the present disclosure.
Figure 8:
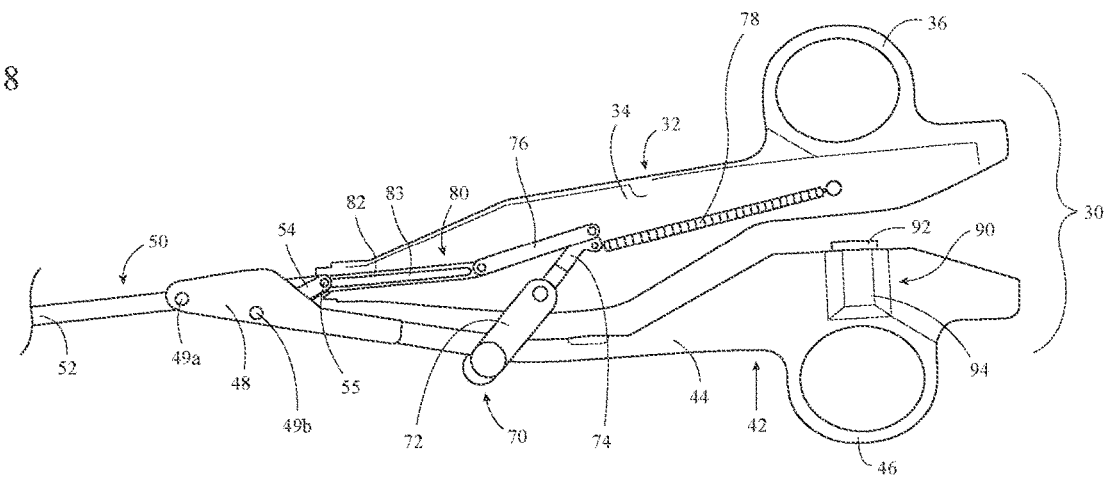
FIG. 8 is a side view of a proximal portion of the forceps of FIG. 1, with the elongated shaft and a portion of a housing of a fixed handle removed.

Turning to FIG. 1, an electrosurgical forceps provided in accordance with the present disclosure is shown generally identified by reference numeral 10. Forceps 10 is configured for use in VATS procedures and other surgical procedures and generally includes an elongated shaft 20, a handle assembly 30, a drive assembly 50 (FIGS. 3A-3C), a trigger assembly 70, a knife assembly 80 (FIGS. 8 and 9), an activation assembly 90, and an end effector assembly 100 which mutually cooperate to grasp, treat, and/or cut tissue. Forceps 10 further includes an electrosurgical cable (not shown) adapted to connect forceps 10 to a source of energy, e.g., a generator (not shown), although forceps 10 may alternatively be configured as a battery-powered instrument.

Figure 2:
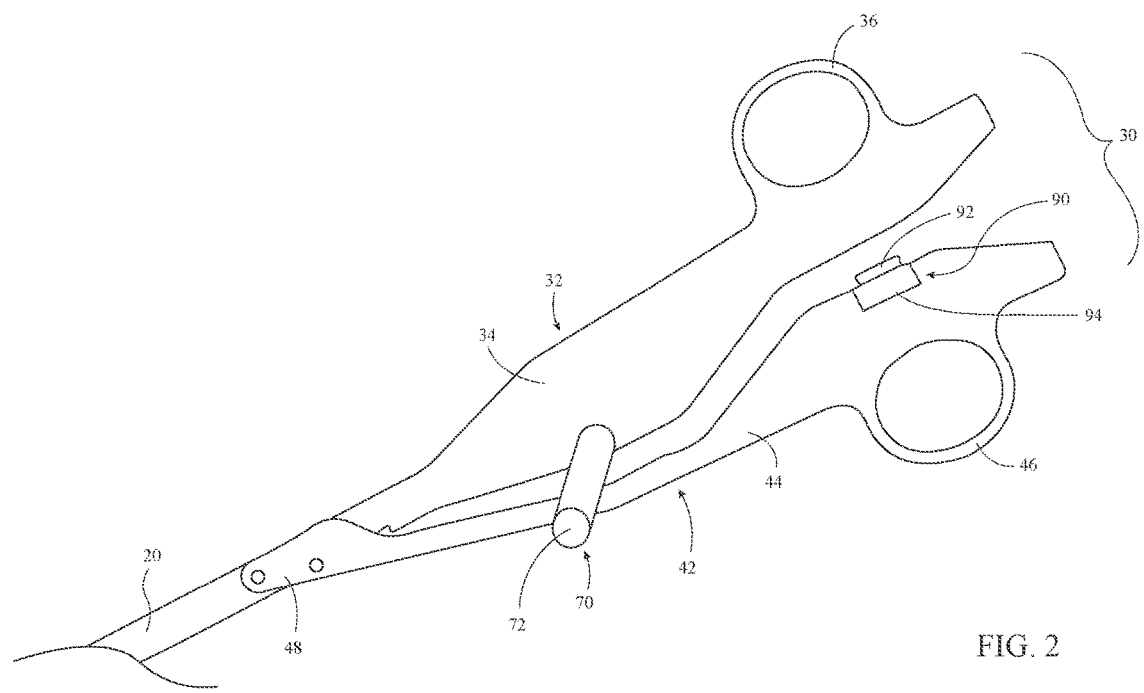
FIG. 2 is a side view of a proximal portion of the forceps of FIG. 1.
Figure 9:
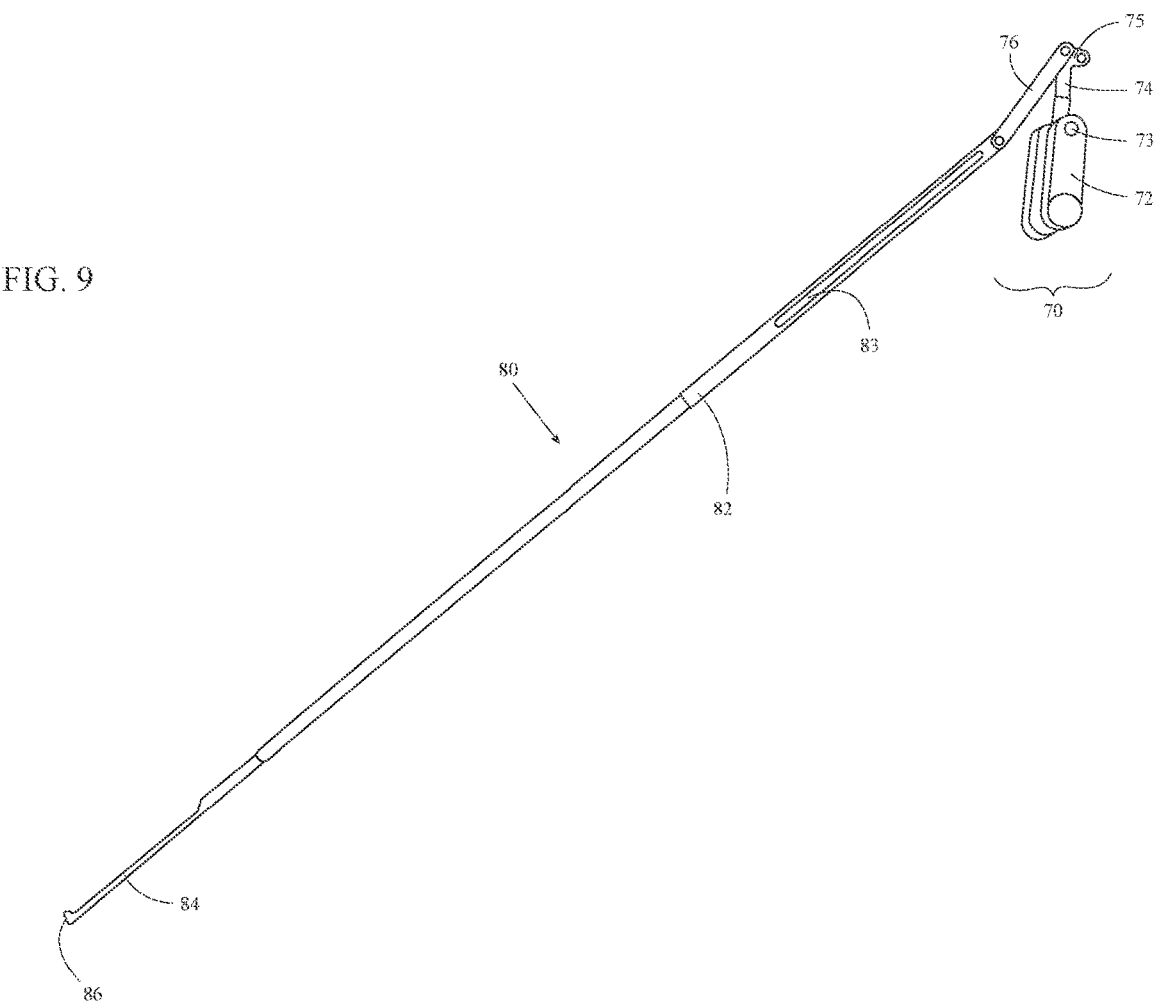
FIG. 9 is a side view of a trigger assembly and a knife assembly of the forceps of FIG. 1.
Figure 10:
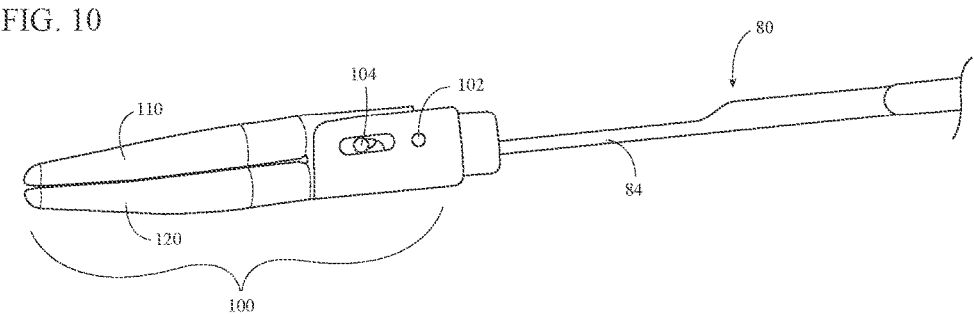
FIG. 10 is a side view of the end effector assembly of the forceps of FIG. 1 including a knife of the knife assembly of FIG. 8 operably positioned relative thereto.
Figure 11:
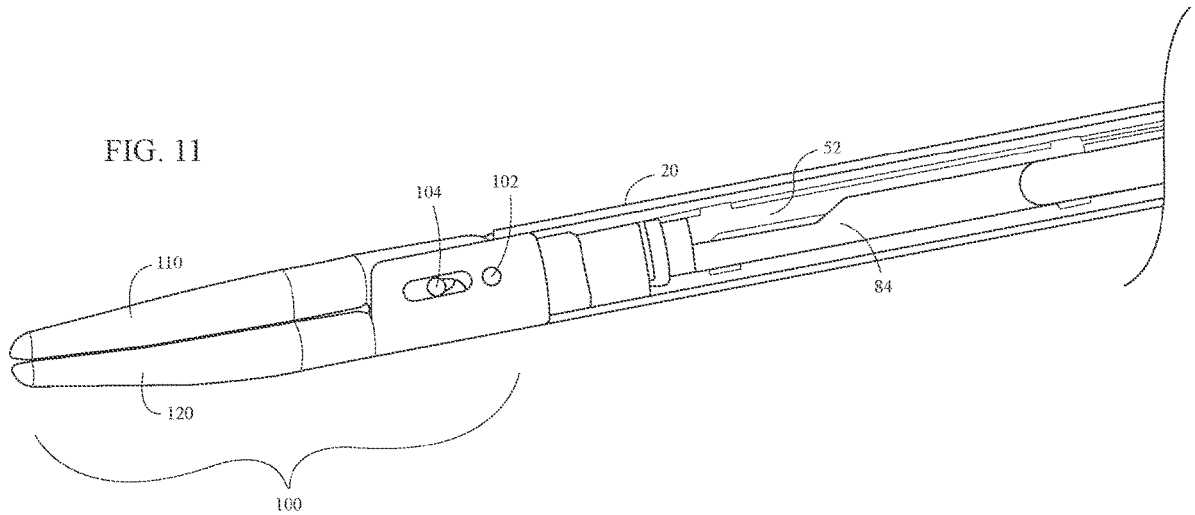
FIG. 11 is a side view of a distal portion of the forceps of FIG. 1, with a portion of the elongated shaft removed.

With additional reference to FIG. 2, handle assembly 30 is operably coupled to a proximal portion of elongated shaft 20 and includes a pair of handle members: a fixed handle 32 and a movable handle 42. Fixed handle 32 is fixedly engaged with elongated shaft 20 and extends proximally therefrom. Fixed handle 32 includes a body 34 formed from first and second housing components that cooperate to house the internal components of trigger assembly 70 (FIG. 8) as well as knife drive bar 82 of knife assembly 80 (FIG. 9). Fixed handle 32 further includes a finger ring 36 disposed on a proximal portion of body 34. Finger ring 36 is configured to receive one or more fingers of a user to facilitate grasping and manipulating forceps 10.

Movable handle 42 of handle assembly 30 includes a body 44 formed from first and second housing components that cooperate to retain activation assembly 90 partially within body 44 and in operable position relative to fixed handle 32, as detailed below. The electrosurgical cable (not shown) of forceps 10 is configured to operably couple to movable handle 42 while the internal wires (not shown) thereof are configured to extend through body 44 of movable handle 42 and elongated shaft 20 to end effector assembly 100 (FIG. 1) to electrically couple end effector assembly 100 (FIG. 1) and activation assembly 90 with the source of energy (not shown). Movable handle 42 further includes a finger ring 46 disposed on a proximal portion of body 44. Finger ring 46 is configured to receive one or more fingers of a user to facilitate grasping and manipulating forceps 10.

Figure 3A:
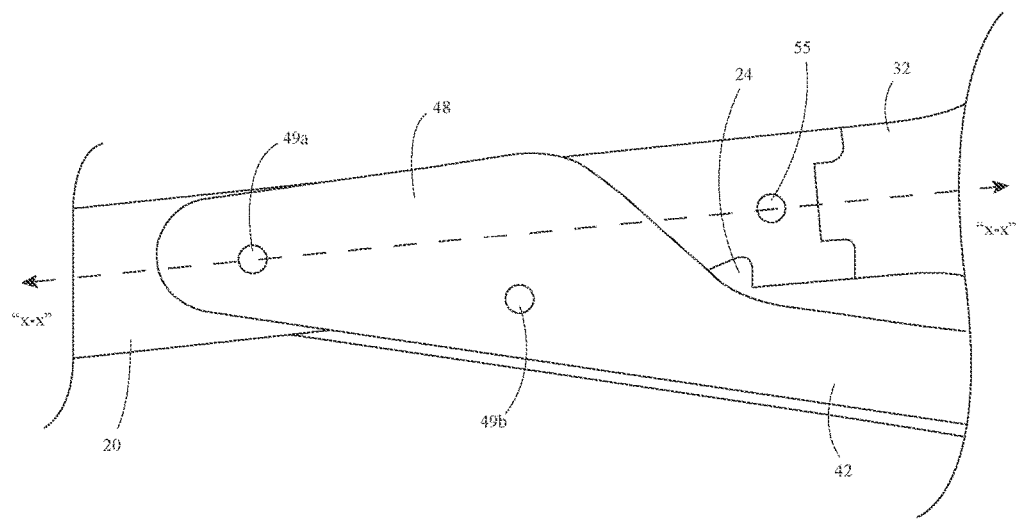
FIG. 3A is an enlarged, side view of the area of detail indicated as "3A" in FIG. 1.
Figure 3B:
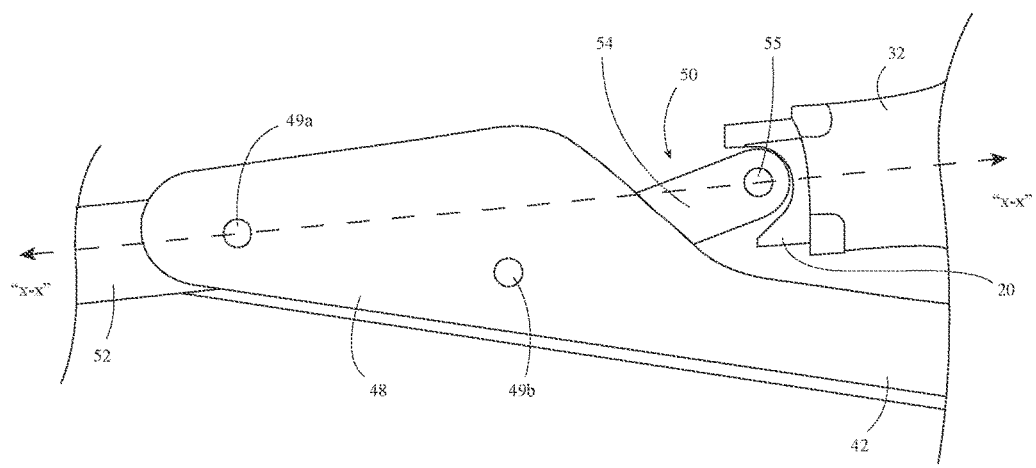
FIG. 3B is an enlarged, side view of the area of detail indicated as "3A" in FIG. 1, with parts removed.
Figure 3C:
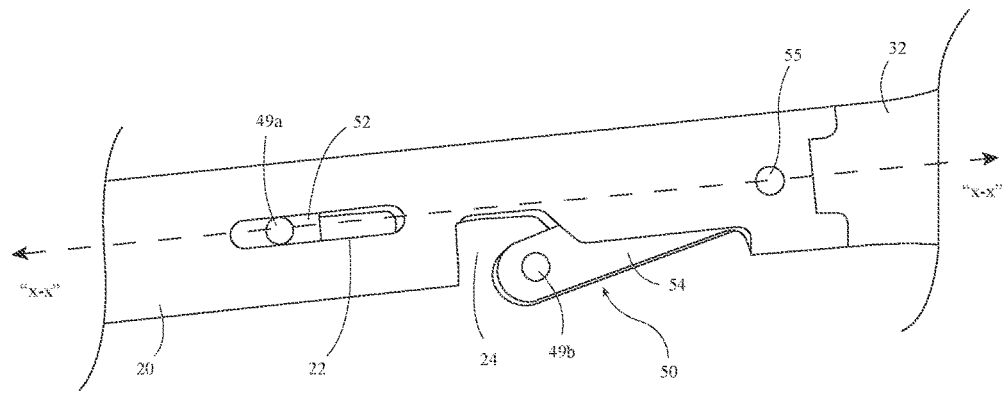
FIG. 3C is an enlarged, side view of the area of detail indicated as "3A" in FIG. 1, with other parts removed.

Referring to FIGS. 3A-3C, movable handle 42 additionally includes a clevis 48 extending distally from a distal portion of body 44. Clevis 48 defines a bifurcated configuration including first and second spaced-apart clevis members. The first and second spaced-apart clevis member of clevis 48 are configured for positioning on either side of elongated shaft 20 such that elongated shaft 20 is at least partially received within clevis 48. Clevis 48 is configured to operably couple movable handle 42 with elongated shaft 20 and drive assembly 50. Distal and proximal pins 49a, 49b are fixed relative to clevis 48 and extend transversely between the first and second spaced-apart clevis members of clevis 48. Distal pin 49a is configured to pivotably couple clevis 48 to a proximal portion of drive bar 52 of drive assembly 50. Elongated shaft 20 defines a pair of opposed slots 22 (only one is shown) through which distal pin 49a extends to enable coupling of clevis 48 and drive bar 52 with elongated shaft 20 disposed therebetween. Proximal pin 49b is configured to pivotably couple clevis 48 to a distal portion of linkage 54 of drive assembly 50. Elongated shaft 20 defines a cut-out 24 configured to enable pivoting of movable handle 42 relative to fixed handle 32 and elongated shaft 20, as detailed below.

Drive assembly 50 of forceps 10, as noted above, includes drive bar 52 and linkage 54. Drive bar 52 is slidably disposed within elongated shaft 20 and includes a proximal portion that is pivotably coupled to clevis 48 of movable handle 42 via distal pin 49a. A distal portion of linkage 54 extends through cut-out 24 of elongated shaft 20 and is pivotably coupled to clevis 48 via proximal pin 49b. A proximal portion of linkage 54 extends through cut-out 24 into elongated shaft 20 and is pivotably coupled to elongated shaft 20 within elongated shaft 20 via a linkage pin 55. Linkage pin 55 and distal pin 49a are both aligned on a longitudinal axis "X-X" of elongated shaft 20.

As a result of the above-detailed configuration of movable handle 42 and drive assembly 50, pivoting of movable handle 42 relative to fixed handle 32 between an open position and a closed position translates drive bar 52 through elongated shaft 20. More specifically, pivoting of movable handle 42 towards fixed handle 32, e.g., towards the closed position, translates drive bar 52 distally through elongated shaft 20, while pivoting of movable handle 42 away from fixed handle 32, e.g., towards the open position, translates drive bar 52 proximally through elongated shaft 20.

As movable handle 42 is pivoted towards the closed position, the distal portion of linkage 54 is pivoted towards an aligned orientation relative to elongated shaft 20 and, thus, proximal pin 49b is moved towards longitudinal axis "X-X" of elongated shaft 20. The configuration of handle assembly 30, elongated shaft 20, and/or drive assembly 50 inhibits linkage 54 from reaching an aligned position relative to longitudinal axis "X-X" of elongated shaft 20 and, thus, inhibits proximal pin 49b from reaching an over-center position relative to linkage pin 55, distal pin 49a, and longitudinal axis "X-X" of elongated shaft 20. As such, movable handle 42 remains freely movable relative to fixed handle 32 and is not locked in position relative thereto, as is the case when an over-center position is achieved.

Despite being inhibited from reaching an over-center position, proximal pin 49b is configured to move at least partially into cut-out 24 of elongated shaft 20 as movable handle 42 is moved to the closed position to achieve a near-over-center position. This near-over-center position reduces the forces necessary to pivot movable handle 42 towards fixed handle 32 as movable handle 42 approaches the closed position without permitting locking of the movable handle 42. The term near-over-center position, for the purposes herein, corresponds to a position wherein proximal pin 49b is disposed at least partially within cut-out 24 of elongated shaft 20 and, thus, is at least partially inside the outer diameter of elongated shaft 20. As such, the near-over-center position of proximal pin 49b corresponds to a radial distance between longitudinal axis "X-X" of elongated shaft 20 and proximal pin 49b that is equal to or less than the radius of elongated shaft 20 plus the diameter of proximal pin 49b. In embodiments where elongated shaft 20 defines a rectangular or other non-cylindrical configuration, the near-over-center position of proximal pin 49b corresponds to a radial distance between longitudinal axis "X-X" of elongated shaft 20 and proximal pin 49b that is equal to or less than half of the corresponding transverse dimension of elongated shaft 20 (taken along a line perpendicular to longitudinal axis "X-X" and intersecting proximal pin 49b) plus the diameter of proximal pin 49b.

Referring to FIGS. 1 and 4-5B, end effector assembly 100 is coupled to a distal portion of elongated shaft 20 and includes first and second jaw members 110, 120. One or both of jaw members 110, 120 is pivotable relative to the other and the elongated shaft 20 about a pivot pin 102. Each jaw member 110, 120 includes a proximal flange 111, 121 and a distal jaw body 112, 122 supporting an electrically-conductive tissue-contacting surface 114, 124. Tissue-contacting surfaces 114, 124 are electrically coupled to activation assembly 90 (FIG. 1) and the source of energy (not shown), e.g., via the wires (not shown) extending through the electrosurgical cable (not shown), movable handle 42, and elongated shaft 20, such that energy may be selectively supplied to tissue-contacting surface 114 and/or tissue-contacting surface 124 and conducted through tissue grasped between jaw members 110, 120 to treat, e.g., seal, tissue.

Proximal flanges 111, 121 of jaw members 110, 120 are pivotably coupled to one another via pivot pin 102. End effector assembly 100 is configured as a unilateral assembly, wherein jaw member 120 is fixed relative to elongated shaft 20 and jaw member 110 is pivotable about pivot pin 102 relative to elongated shaft 20 and fixed jaw member 120. However, end effector assembly 100 may alternatively be configured as a bilateral assembly, where both jaw member 110 and jaw member 120 are movable about pivot pin 102 relative to one another and elongated shaft 20. For the purposes herein, the terms "movement of the jaw members," "pivoting of the jaw members," and like terms are understood to encompass both unilateral and bilateral configurations. In the illustrated unilateral configuration, proximal flange 121 of jaw member 120 may be fixedly engaged to elongated shaft 20 via welding or other suitable engagement. Pivot pin 102 may be welded, on either side thereof, to proximal flange 121 of jaw member 120 and pivotably disposed within an aperture defined through proximal flange 111 of jaw member 110. Other configurations are also contemplated, for example, using a clip similar to that detailed below with respect to cam pin 104 and clip 106 (FIGS. 6A-6B).

Proximal flanges 111, 121 of jaw members 110, 120 define oppositely-oriented U-shaped configurations. One of the proximal flanges, e.g., proximal flange 121 of jaw member 120, may surround the proximal flange, e.g., proximal flange 111 of jaw member 110, of the other jaw member, as illustrated (see FIG. 6A). Alternatively, proximal flanges 111, 121 may be disposed in an overlapping, offset configuration. Each proximal flange 111, 121 defines a pair of cam slots 116, 126 therethrough. Cam slots 116 of proximal flange 111 of jaw member 110 are angled relative to cam slots 126 of proximal flange 121 of jaw member 120. Cam slots 116, 126 are configured to receive a cam pin 104 that extends through an aperture defined through a distal portion of drive bar 52. As a result of this configuration, translation of drive bar 52 through elongated shaft 20, e.g., in response to pivoting of movable handle 42 (FIG. 1) between the open an closed positions, pivots jaw members 110, 120 between spaced-apart and approximated positions for grasping tissue therebetween. More specifically, cam slots 116, 126 are oriented such that distal translation of drive bar 52 and, thus, cam pin 104, effects pivoting of jaw members 110, 120 from the spaced-apart position towards the approximated position, and such that proximal translation of drive bar 52 and, thus, cam pin 104 pivots jaw members 110, 120 towards the spaced-apart position.

Figure 6A:
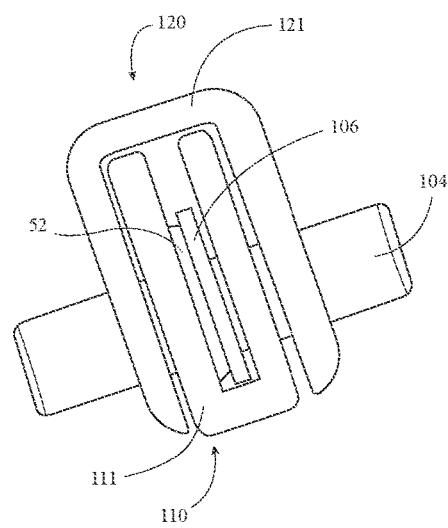
FIG. 6A is a transverse, cross-sectional view of an end effector assembly of the forceps of FIG. 1.
Figure 6B:
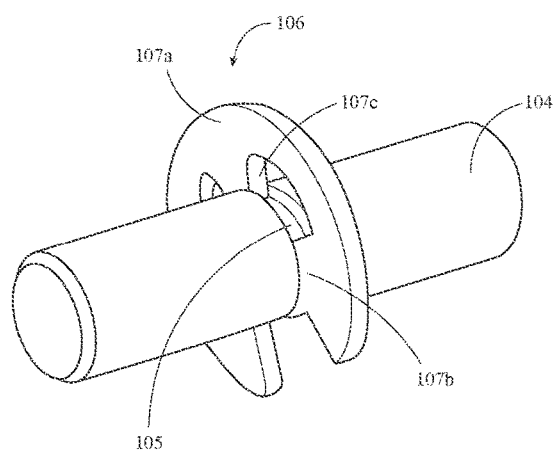
FIG. 6B is a perspective view of a cam pin of the end effector assembly of FIG. 6A including a clip engaged about the cam pin.

Referring to FIGS. 6A and 6B, a clip 106 is provided to operably couple cam pin 104 with jaw members 110, 120 and drive bar 52, and to retain cam pin 104 in position without the need for welding (or otherwise affixing) cam pin 104 to drive bar 52. Such a configuration is advantageous in that welding (or otherwise affixing) cam pin 104 to drive bar 52 is difficult due to the necessity for drive bar 52 to be operably positioned between jaw members 110, 120 and cam pin 104 inserted therebetween prior to welding cam pin 104 thereto.

Clip 106 includes a body 107a having a pair of resilient, semi-annular side fingers 107b (only one is shown) extending from either side thereof and a central finger 107c extending between side fingers 107b. Cam pin 104 defines an annular groove 105 to facilitate engagement of clip 106 thereabout. Side fingers 107b, at the free ends thereof and in their at-rest position, are spaced-apart a distance smaller than the diameter of the portion of clip 106 that defines groove 105.

In order to operably couple jaw members 110, 120 and drive bar 52 with one another via cam pin 104, jaw members 110, 120 are first aligned such that cam slots 116, 126 of proximal flanges 111, 121 of jaw members 110, 120, respectively, are aligned with one another. Drive bar 52 is inserted between proximal flanges 111, 121 such that the aperture defined within drive bar 52 is aligned with cam slots 116, 126. Once cam slots 116, 126 are aligned with one another and the aperture of drive bar 52, cam pin 104 may be inserted, from either side of end effector assembly 100, through cam slots 116, 126 and the aperture of drive bar 52. In the inserted position of cam pin 104, groove 105 is exposed between between drive bar 52 and flanges 111, 121 to enable distal insertion of clip 106 between drive bar 52 and flanges 111, 121 and into engagement with cam pin 104.

In order to engage clip 106 about cam pin 104, clip 106 is aligned with groove 105 of cam pin 104 and moved transversely towards clip 106. As clip 106 is moved into contact with cam pin 104, side fingers 107b contact the inner surface of can pin defining groove 105 and are flexed outwardly relative to one another to widen the gap therebetween and permit cam pin 104 to pass therebetween. Once cam pin 104 is positioned more than halfway within clip 106, e.g., once side fingers 107b clear the diameter of cam pin 104, side fingers 107b are returned under bias inwardly into engagement within groove 105, thereby retaining clip 106 about cam pin 104. Upon engagement of clip 106 about cam pin 104, central finger 107c is also disposed within groove 105.

With clip 106 engaged about cam pin 104, cam pin 104 is inhibited from sliding laterally out of engagement with cam slots 116, 126 and/or the aperture of drive bar 52. Thus, cam pin 104 is retained in operable engagement within cam slots 116, 126 and the aperture of drive bar 52 such that translation of drive bar 52 relative to end effector assembly 100 translates cam pin 104 through cam slots 116, 126 to pivot jaw members 110, 120 between the spaced-apart and approximated positions.

Figure 4:
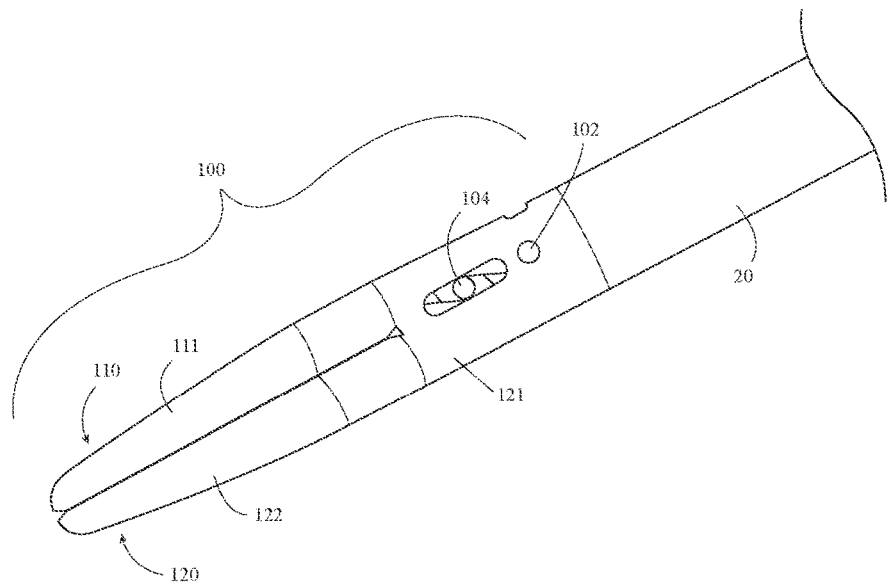
FIG. 4 is a side view of a distal portion of the forceps of FIG. 1.
Figure 5A:
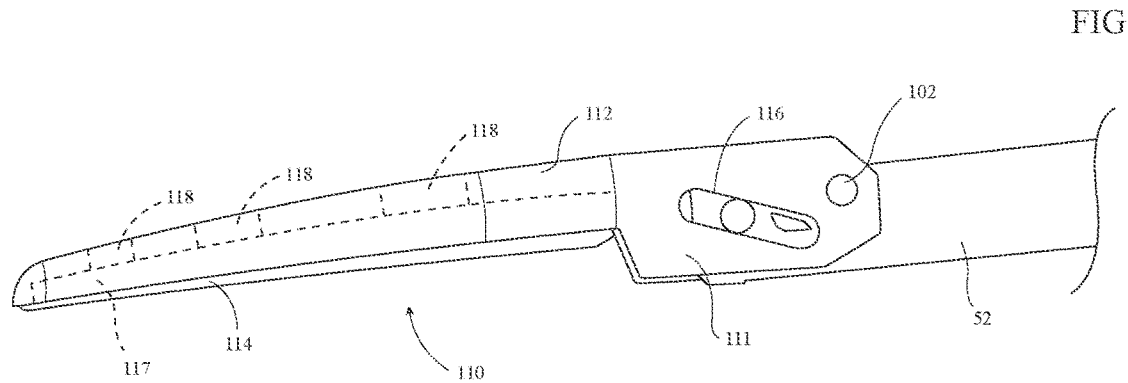
FIG. 5A is a side view of the distal portion of the forceps of FIG. 1, with an elongated shaft and one jaw member removed.
Figure 5B:
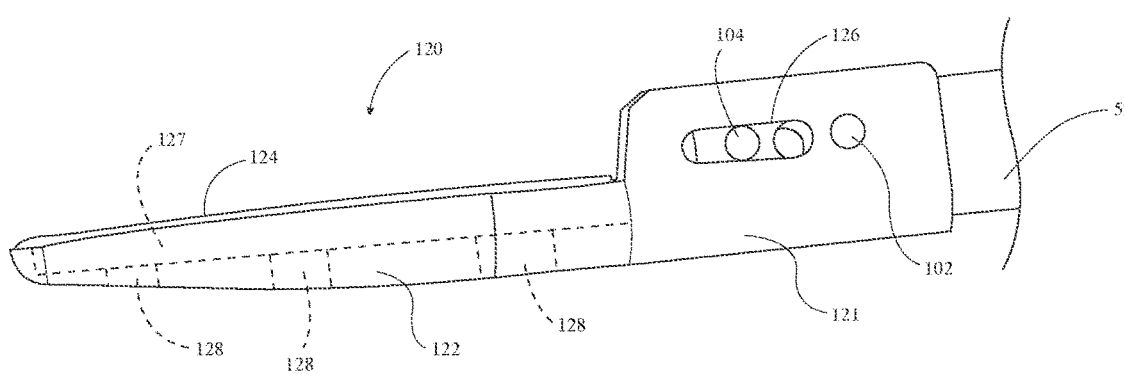
FIG. 5B is a side view of the distal portion of the forceps of FIG. 1, with the elongated shaft and another jaw member removed.

With reference to FIGS. 4-5B, distal jaw bodies 112, 122 of jaw members 110, 120 extend distally from proximal flanges 111, 121, respectively, and, as noted above, support respective electrically-conductive tissue-contacting surfaces 114, 124 thereon. Distal jaw bodies 112, 122 and, thus, tissue-contacting surfaces 114, 124, define curved configurations, although other configurations may also be provided. In the approximated position of jaw members 110, 120, tissue-contacting surfaces 114, 124 are configured to grasp tissue therebetween and, upon activation of activation assembly 90 (FIG. 1), conduct energy therebetween and through grasped tissue to treat, e.g., seal, tissue. Either or both tissue-contacting plates 114, 124 may further define a longitudinally-extending knife channel 117, 127 extending therethrough. Knife channel(s) 117, 127 are configured to receive a knife 84 of knife assembly 80 (FIG. 9) to facilitate reciprocation of knife 84 (FIG. 9) between jaw members 110, 120 to cut tissue disposed therebetween, e.g., upon actuation of rotatable trigger 72 of trigger assembly 70 (see FIG. 9).

Figure 7:
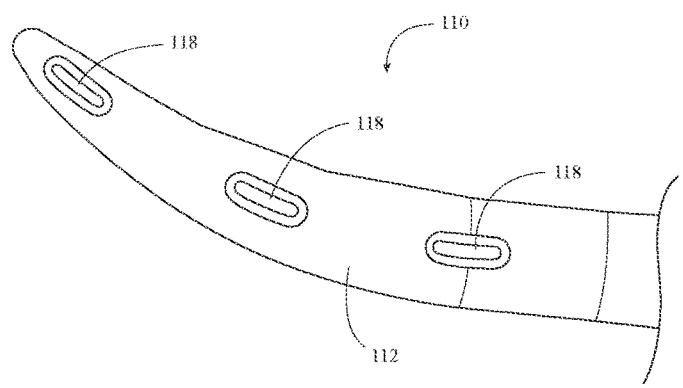
FIG. 7 is a top view of one of jaw members of the end effector assembly of the forceps of FIG. 1.

Referring additionally to FIG. 7, the distal jaw body 112, 122 of one or both of jaw members 110, 120 further includes a plurality of vent holes 118, 128 defined therethrough (only vent holes 118 of jaw member 110 are shown in FIG. 7; the vent holes of jaw member 120 may be similar in embodiments where so provided). Vent holes 118, 128 are arranged longitudinally along jaw member 110 and extend completely through distal jaw bodies 112, 122. More specifically, vent holes 118, 128 are aligned with and disposed in communication with knife channels 117, 127 of jaw members 110, 120. As such, steam generated during tissue treatment may escape the area between jaw members 110, 120 via knife channels 117, 127 and vent holes 118, 128.

Turning to FIGS. 8-11, trigger assembly 70 and knife assembly 80 cooperate to enable selective deployment of knife 84 between a retracted position, wherein knife 84 is disposed proximally of jaw members 110, 120, and an extended position, wherein knife 84 extends at least partially through knife channels 117, 127 (FIGS. 5A-5B) between jaw members 110, 120. Trigger assembly 70 is operably coupled to and partially disposed within body 34 of fixed handle 32. Trigger assembly 70 includes a rotatable trigger 72, a first linkage 74, a second linkage 76, and a spring 78. Rotatable trigger 72 defines a bifurcated configuration and extends from body 34 of fixed handle 32 towards movable handle 42. In the closed position of handle assembly 30, the bifurcated rotatable trigger 72 at least partially surrounds body 44 of movable handle 42, thus enabling actuation of rotatable trigger 72 from either side of forceps 10 (FIG. 1). Rotatable trigger 72 is pivotably coupled to fixed handle 32 about a pivot 73.

First linkage 74 of trigger assembly 70 is disposed within body 34 of fixed handle 32. First linkage 74 is pivotably coupled to fixed handle 32 about pivot 73 towards a first end of first linkage 74 and is engaged with rotatable trigger 72 such that pivoting of rotatable trigger about pivot 73 likewise pivots first linkage 74 about pivot 73. The second end of first linkage 74 defines a Y-connector 75. Spring 78 is disposed within body 34 of fixed handle 32 and includes a first end that is fixed relative to body 34 and a second end that is engaged with one of the prongs of Y-connector 75. Spring 78 is configured to bias first linkage 74 and, thus, rotatable trigger 72, towards an un-actuated position. Spring 78 also biases knife 84 towards the retracted position.

Second linkage 76 operably couples first linkage 74 and, thus rotatable trigger 72, with knife assembly 80. More specifically, second linkage 76 is coupled to the other prong of Y-connector 75 of first linkage 74 towards the proximal end of second linkage 76, and is coupled to a proximal portion of knife drive bar 82 towards the distal end of second linkage 76. As a result, pivoting of rotatable trigger 72 about pivot 73 pivots first linkage 74 about pivot 73 to urge second linkage 76 distally through body 34 of fixed handle 32.

Knife assembly 80 includes knife drive bar 82 and knife 84. A proximal portion of knife drive bar 82 is pivotably coupled to a distal portion of second linkage 76, and a distal portion of knife drive bar 82 is fixedly engaged with a proximal portion of knife 84 with knife 84 extending distally therefrom. Knife drive bar 82 defines a slot 83 configured to receive distal pin 49*a* and linkage pin 55 (see FIGS. 3A-3C) to enable knife drive bar 82 to slide relative thereto. Knife 84 defines a distal cutting edge 86. In operation, pivoting of rotatable trigger 72 from an un-actuated position to an actuated position pivots first linkage 74 to urge second linkage 76 distally through body 34 of fixed handle 32, thereby urging knife drive bar 82 distally through elongated shaft 20 and translating knife 84 from the retracted position to the extended position. Release of rotatable trigger 72 returns rotatable trigger 72 back towards the un-actuated position under the bias of spring 78, thereby returning first linkage 74, second linkage 76, and knife drive bar 82 such that knife 84 is returned to the retracted position.

Referring again to FIGS. 1 and 2, activation assembly 90, as noted above, is at least partially retained within body 44 of movable handle 42. Activation assembly 90 includes an activation button 92 and a base 94. Activation button 92 is selectively depressible relative to base 94 to initiate the supply of energy to tissue-contacting surfaces 114, 124 of jaw members 110, 120 (see FIGS. 5A-5B), respectively. More specifically, upon achieving the fully closed position of handle assembly 30, activation button 92 is urged into the opposed surface of body 34 of fixed handle 32 so as to depress activation button 92 and initiate the supply of energy to tissue-contacting surfaces 114, 124 of jaw members 110, 120 (see FIGS. 5A-5B).

The various aspects and features provided herein may also be configured to work with robotic surgical systems and what is commonly referred to as "Telesurgery." Such systems employ various robotic elements to assist the surgeon in the operating room and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments provided herein while another surgeon (or group of surgeons) remotely control the instruments via the robotic surgical system. As can be appreciated, a highly skilled surgeon may perform multiple operations in multiple locations without leaving the remote console, which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the aspects and features described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting, or treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly of an electrosurgical instrument, comprising:
   first and second jaw members each including a proximal flange portion and a distal body portion, the distal body portions of the first and second jaws members defining tissue-contacting surfaces, the proximal flange portions of the first and second jaw members pivotably coupled to one another such that at least one of the first or second jaw members is movable relative to the other between spaced-apart and approximated positions for grasping tissue between the tissue-contacting surfaces, the proximal flange portions of the first and second jaw members each defining a cam slot;

a cam pin extending through the cam slots of the first and second jaw members and configured to slide through the cam slots to move the at least one of the first or second jaw members between the spaced-apart and approximated positions; and a clip engaged with the cam pin to retain the cam pin within the cam slots of the first and second jaw members, wherein the cam pin defines an annular groove configured to receive a portion of the clip.

2. The end effector assembly according to claim 1, wherein each proximal flange portion is bifurcated such that the first and second jaw members each define a pair of spaced-apart proximal flange components, the proximal flange components of the first jaw member defining aligned cam slot segments that cooperate to define the cam slot of the first jaw member and the proximal flange components of the second jaw member defining aligned cam slot segments that cooperate to define the cam slot of the second jaw member.

3. The end effector assembly according to claim 2, wherein proximal flange components of the first jaw member are disposed between the proximal flange components of the second jaw member.

4. The end effector assembly according to claim 3, wherein the clip is disposed between the proximal flange components of the first jaw member.

5. The end effector assembly according to claim 2, wherein proximal flange components of the first and second jaw members are disposed in offset, overlapping relation relative to one another.

6. The end effector assembly according to claim 5, wherein the clip is disposed between one of the proximal flange components of the first jaw member and one of the proximal flange components of the second jaw member.

7. The end effector assembly according to claim 1, wherein the clip includes a pair of side fingers and a central finger disposed between the side fingers, each of the side fingers and the central finger configured for engagement within the annular groove of the cam pin.

8. An electrosurgical instrument, comprising:

a shaft;

a drive bar extending through the shaft; and an end effector assembly disposed at a distal end portion of the shaft, the end effector assembly including;

first and second jaw members each including a proximal flange portion and a distal body portion, the distal body portions of the first and second jaws members defining tissue-contacting surfaces, the proximal flange portions of the first and second jaw members pivotably coupled to one another and at least one of the proximal flange portions pivotably coupled to the shaft such that at least one of the first or second jaw members is movable relative to the other and the shaft between spaced-apart and approximated positions for grasping tissue between the tissue-contacting surfaces, the proximal flange portions of the first and second jaw members each further defining a cam slot;

a cam pin extending through the cam slots of the first and second jaw members, wherein the drive bar is engaged about the cam pin such that translation of the drive bar slides the cam pin through the cam slots to move the at least one of the first or second jaw members between the spaced-apart and approximated positions; and a clip engaged with the cam pin to retain the cam pin within the cam slots of the first and second jaw members, wherein the cam pin defines an annular groove configured to receive a portion of the clip.

9. The electrosurgical instrument according to claim 8, wherein each proximal flange portion is bifurcated such that the first and second jaw members each define a pair of spaced-apart proximal flange components, the proximal flange components of the first jaw member defining aligned cam slots segments that cooperate to define the cam slot of the first jaw member and the proximal flange components of the second jaw member defining aligned cam slot segments that cooperate to define the cam slot of the second jaw member.

10. The electrosurgical instrument according to claim 9, wherein proximal flange components of the first jaw member are disposed between the proximal flange components of the second jaw member.

11. The electrosurgical instrument according to claim 10, wherein the clip is disposed between the proximal flange components of the first jaw member.

12. The electrosurgical instrument according to claim 10, wherein the drive bar is engaged about the cam pin between the proximal flange components of the first jaw member.

13. The electrosurgical instrument according to claim 9, wherein proximal flange components of the first and second jaw members are disposed in offset, overlapping relation relative to one another.

14. The electrosurgical instrument according to claim 13, wherein the clip is disposed between one of the proximal flange components of the first jaw member and one of the proximal flange components of the second jaw member.

15. The electrosurgical instrument according to claim 13, wherein the drive bar is engaged about the cam pin between one of the proximal flange components of the first jaw member and one of the proximal flange components of the second jaw member.

16. The electrosurgical instrument according to claim 1, wherein the clip includes a pair of side fingers and a central finger disposed between the side fingers, each of the side fingers and the central finger configured for engagement within the annular groove of the cam pin.

\* \* \* \* \*